(12) United States Patent
Castillo Sancho et al.

(10) Patent No.: US 9,718,071 B2
(45) Date of Patent: Aug. 1, 2017

(54) MULTIFUNCTIONAL SPRAY MACHINE FOR COLD MACRO- AND MICRO-SPRAY

(71) Applicants: Fernando Castillo Sancho, Utebo (ES); Igor Rodriguez Sanchez, Gabarderal (ES)

(72) Inventors: Fernando Castillo Sancho, Utebo (ES); Igor Rodriguez Sanchez, Gabarderal (ES)

(*) Notice: Subject to any disclaimer, the term of this patent is extended or adjusted under 35 U.S.C. 154(b) by 380 days.

(21) Appl. No.: 13/915,634

(22) Filed: Jun. 12, 2013

(65) Prior Publication Data
US 2014/0367491 A1 Dec. 18, 2014

(51) Int. Cl.
| | |
|---|---|
| *A61M 11/02* | (2006.01) |
| *B05B 9/04* | (2006.01) |
| *B05B 7/24* | (2006.01) |
| *A61L 9/14* | (2006.01) |
| *B05B 1/16* | (2006.01) |
| *B05B 7/00* | (2006.01) |

(52) U.S. Cl.
CPC .............. *B05B 7/2491* (2013.01); *A61L 9/14* (2013.01); *B05B 1/16* (2013.01); *B05B 7/0012* (2013.01); *B05B 7/2424* (2013.01); *A61L 2209/134* (2013.01)

(58) Field of Classification Search
CPC ....... B05B 7/2491; B05B 7/2424; B05B 1/16; A61L 9/14; A61L 2209/134
USPC ......... 239/69, 332, 333, 373, 338, 340, 369, 239/390; 222/152, 401
See application file for complete search history.

(56) References Cited

U.S. PATENT DOCUMENTS

| | | | | |
|---|---|---|---|---|
| 6,032,407 | A * | 3/2000 | Conner | 43/129 |
| 7,178,743 | B2 * | 2/2007 | Clarke et al. | 239/304 |
| 2007/0173980 | A1 * | 7/2007 | Lovett et al. | 700/283 |
| 2008/0153408 | A1 * | 6/2008 | Thomas | 454/156 |
| 2008/0262650 | A1 * | 10/2008 | Dorendorf et al. | 700/240 |
| 2009/0056009 | A1 * | 3/2009 | Matsubara et al. | 4/524 |
| 2009/0324504 | A1 * | 12/2009 | Sen | 424/43 |
| 2012/0187210 | A1 * | 7/2012 | Wheeler et al. | 239/8 |

FOREIGN PATENT DOCUMENTS

JP 08229094 A * 9/1996

* cited by examiner

*Primary Examiner* — Kristen Matter
(74) *Attorney, Agent, or Firm* — Lucas & Mercanti, LLP

(57) ABSTRACT

The invention proposed refers to a Multifunctional cold macro- and micro-spray spraying machine, techniques known as "coldspraying" and "coldfogging" done automatically and independently by a single spray machine, making it a multifunctional spray machine able to perform shock treatments and to maintain atmospheric deinsecting, disinfection, deodorizing and odorizing depending on the liquid formulation of active agents dosed.

3 Claims, 1 Drawing Sheet

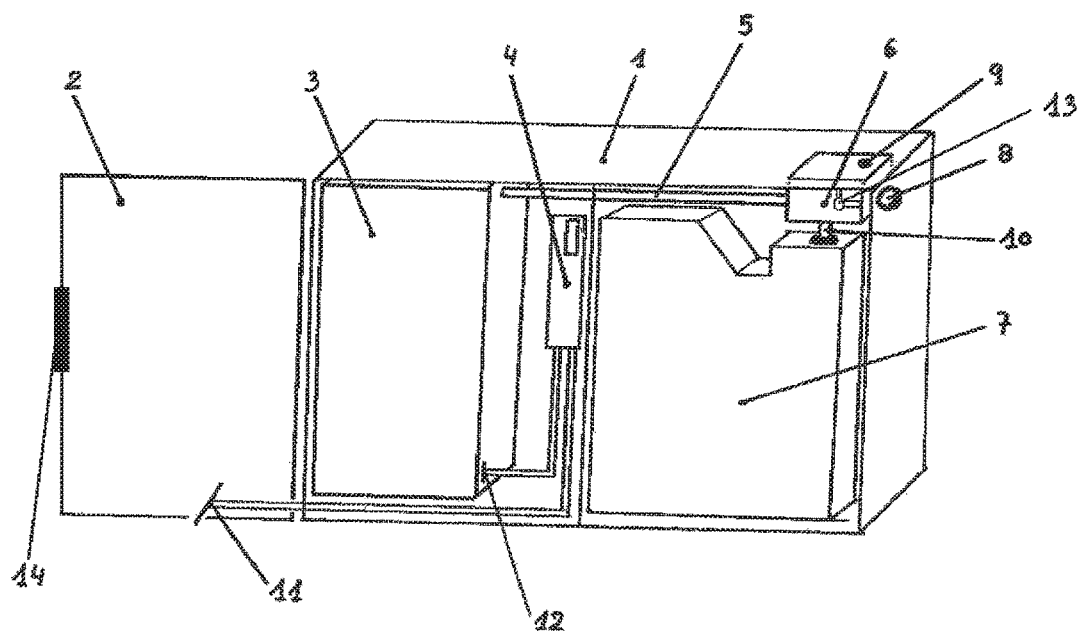

MULTIFUNCTIONAL SPRAY MACHINE FOR COLD MACRO- AND MICRO-SPRAY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Technical Field

The Field of the invention is that of manufacturers of air conditioning machines tools and atmospheric treatment machines.

Description of the Related Art

There are some antecedents of the system described in these specifications, but all of them for deinsecting, disinfection, deodorising and air treatments, using large, manual machines where an operator doses gasified compounds specifically and in focused form.

This diffusion of gasified and/or nebulised emissions is for application only in shock treatments where a plague and/or infestation is already established, and is done manually and in person because the machines are neither automatic nor autonomous, nor does their range extend beyond a few hours' use.

Such doses mean that the area to be treated must be evacuated completely as these gasified and/or nebulised compounds are harmful to humans in the doses designed for those machines and because of the chemical compounds based on biocides, germicides, insecticides, etc. . . . , making it indispensable for qualified technical personnel to be present to handle them.

Said machines are designed for one function only, the manual dosing of biocides, germicides, insecticides and various chemical compounds, most of them toxic to humans and leading to problems of atmospheric pollution. They have large tanks because their consumption of the chemical compounds dosed is high, so limiting their range of use to short periods of time, usually a few hours' operation.

The proposed invention resolves all these problems as it is a machine which makes it possible to apply shock treatments and environmental maintenance with just one machine, simply altering the mechanical configuration of the spray nozzle and its electronic programming, during a maximum period of 60 days with a single machine and one reload only, of 800 milliliters, to treat an area of up to 1,000 square meters.

The inventor is unaware of any predecessor incorporating the elements of this invention, or the advantages thereof.

BRIEF SUMMARY OF THE INVENTION

The proposed invention refers to a Multifunctional spray machine for cold macro- and micro-spraying known as "coldspraying" and "coldfogging" techniques, done automatically and independently by a single spray machine.

This is thus a multifunctional spray machine able to apply shock treatments and maintain atmospheric deinsecting, disinfection, deodorising and odorising depending on the liquid formulation of the active agents dosed, and combining the macro- and micro-spray settings, enabling it to obtain the specific liquid formulations of active agents developed for the purposes with maximum effectiveness.

More specifically, the spray machine proposed in the invention comprises a box-like housing-frame containing a sliding door with a security seal, inside which there is the operational mechanical assembly made up of a blow pump, a programmable electronic device, a spray nozzle with a two-setting switching valve and a polypropylene tank holding the liquid formulation of specific active agents.

The programmable electronic device is electrically connected to the mains through the connect on and, in parallel, to the blow pump through a connection pipe.

The twin-function spray nozzle has a two-setting switching valve, one for Macro-spray where the air is introduced by the blow pump through a hose connected to the entrance of the spray nozzle and where the amount of air propelled produces a depression inside it, creating suction for the specific liquid formulation of active agents which, mixed with the air propelled, emerges in a heavy drizzle through the spray nozzle spray cone, dosed into the atmosphere through the Macro-spray nozzle on the side of the housing-frame.

On the micro-spray setting, the air is introduced by the blow pump along a hose connected to the spray nozzle entrance and where the amount of air propelled produces a depression inside which creates suction for the specific liquid formulation of active agents which, mixed with the air propelled, emerges as a heavy drizzle through the spray cone via the micro-spray nozzle.

BRIEF DESCRIPTION OF THE DRAWINGS

For a better understanding of the invention, a page of plans is attached, showing the following:

The FIGURE shows a diagrammatic view of the interior of the spray machine.

And in said FIGURE, with the same reference, identical elements are defined, among which the following may be distinguished:

(1).—housing-frame
(2).—housing-frame door
(14).—housing-frame lock
(3).—blow pump
(4).—programmable electronic device
(5).—air pressure duct
(6).—spray nozzle
(7).—tank
(8).—macro-spray nozzle
(9).—micro-spray nozzle
(10).—connecting hose
(11).—electrical mains connection
(12).—blow pump connection
(13).—switching valve

DETAILED DESCRIPTION OF THE INVENTION

Description of the Preferred Embodiment

The invention proposed refers to a Multifunctional cold macro- and micro-spray spraying machine using techniques known as "coldspraying" and "coldfogging", done automatically and independently by a single spray machine.

This makes it a multifunctional spray machine able to perform shock treatments and to maintain atmospheric deinsecting, disinfection, deodorising and odorising depending on the liquid formulation of the active agents dosed, and combining the macro- and micro-spray settings enabling it to dose with maximum effectiveness the specific active agent liquid formulations developed for the purposes.

More specifically, the spray machine proposed in the invention is constituted from a box-like housing-frame (1) containing a sliding door (2) with a security seal (14).

Inside, it houses the operational mechanical assembly comprising at least the following elements:
a blow pump (3),
a programmable electronic device (4),
an air pressure connector,
a spray nozzle (6) with
a two-setting switching valve (13)
a polypropylene tank (7) containing the liquid formulation of specific active agents and which is extended with
an air-connection hose (10) inserted through the mouth of tank (7) until submerged in the solution of the liquid formulation of specific active agents inside said tank.

The programmable electronic device (4) is connected electrically to the mains through connection (11) and in parallel to the blow pump via connection (12).

The twin-function spray Nozzle (6) has a two-setting switching valve.

On the Macro-spray setting, the air is introduced by the blow pump (3) through the hose (5) connected to the spray nozzle entrance (6) where the amount of air propelled causes a depression inside to create the suction of the specific liquid formulation of active agents which, mixed with the air propelled, emerges as a heavy drizzle through the spray cone of the spray nozzle, dosed into the atmosphere through the Macro-spray mouth (8) on the side of the housing-frame.

On the micro-spray setting, the air is introduced by the blow pump (3) through the hose (5) connected to the spray nozzle entrance (6) and the amount of air propelled causes a depression inside to create the suction of the specific liquid formulation of active agents which, mixed with the air propelled, emerges as a heavy drizzle through the spray cone via the micro-spray mouth (9).

Having sufficiently described the nature of the invention and the means for putting it into practice, it must be recorded that the foregoing arrangements and shown in the attached drawings may undergo modifications of detail as long as that does not alter their fundamental principles defined in the preceding paragraphs and summarised in the following claims.

The invention claimed is:

1. A multifunctional machine for cold macro-spraying and micro-spraying comprising:
    a box-like housing frame having a sliding door and a housing frame lock, inside the box-like housing frame, the housing frame comprises:
    a tank holding a liquid formulation;
    an air-connection hose inserted through a mouth of the tank and submerged in the liquid formulation inside the tank;
    a programmable electronic device connected to mains through an electrical mains connection;
    a blow pump;
    a blow pump connection running parallel to the electrical mains connection, at one end being connected to the blow pump and at an opposite end being connected to the programmable electronic device;
    a twin-function spray nozzle having a two-setting switching valve, a first setting being a macro-spray setting for cold spraying through a macro-spray nozzle and a second setting being for a micro-spray setting for cold fogging through a micro-spray nozzle; and
    an air pressure duct connecting the blow pump and the spray nozzle.

2. The multifunctional machine according to claim 1, wherein the switching valve is turned to the first setting, the macro-spray setting for cold spraying, by having air introduced by the blow pump through the air pressure duct connected to the entrance of the spray nozzle and where the air propelled produces a depression inside the spray nozzle creating a suction for suctioning the liquid formulation inside the tank holding the liquid formulation through the connecting hose and mixing with the air propelled thereby emerging in a heavy drizzle through the macro-spray nozzle for cold spraying.

3. The multifunctional machine according to claim 1, wherein the switching valve is turned to the second setting, the micro-spray setting for cold fogging, by having air introduced by the blow pump through the air pressure duct connected to the entrance of the spray nozzle and where the air propelled produces a depression inside the spray nozzle creating a suction for suctioning the liquid formulation inside the tank holding the liquid formulation through the connecting hose and mixing with the air propelled thereby emerging in a heavy drizzle through the micro-spray nozzle for cold fogging.

* * * * *